United States Patent [19]

Edwards et al.

[11] 4,350,826

[45] Sep. 21, 1982

[54] PROCESS FOR PREPARING P-HYDROXY PHENYLGLYCINE

[75] Inventors: Philip N. Edwards; Michael E. McMenim, both of Macclesfield, England

[73] Assignee: Imperial Chemical Industries Limited, London, England

[21] Appl. No.: 215,872

[22] Filed: Dec. 12, 1980

Related U.S. Application Data

[63] Continuation of Ser. No. 925,625, Jul. 17, 1978, abandoned.

[51] Int. Cl.$^3$ ............................................. C07C 99/00
[52] U.S. Cl. .................................................... 562/444
[58] Field of Search ........................................ 562/444

[56] References Cited

U.S. PATENT DOCUMENTS

| | | | |
|---|---|---|---|
| 3,000,888 | 9/1961 | Biekert | 562/444 |
| 3,860,631 | 1/1975 | Gleason et al. | 562/444 |
| 4,105,690 | 8/1978 | Christidis et al. | 562/444 |

FOREIGN PATENT DOCUMENTS

| | | | |
|---|---|---|---|
| 2205895 | 5/1974 | France | 562/444 |
| 1353612 | 5/1974 | United Kingdom | 562/444 |
| 1371896 | 10/1974 | United Kingdom | 562/444 |
| 1377243 | 12/1974 | United Kingdom | 562/444 |

OTHER PUBLICATIONS

Shukla et al., Chem. Abst., vol. 81, p. 472, #19876c (1974).
Faliadi et al., Chem. Abst., vol 81, p. 401, #25278g (1974).

*Primary Examiner*—Natalie Trousof
*Assistant Examiner*—James H. Reamer
*Attorney, Agent, or Firm*—Cushman, Darby & Cushman

[57] ABSTRACT

The disclosure relates to a process for converting p-hydroxymandelic acid or a salt thereof to p-hydroxyphenylglycine. The product is a useful intermediate in the pharmaceutical industry.

12 Claims, No Drawings

PROCESS FOR PREPARING P-HYDROXY PHENYLGLYCINE

This is a continuation of application Ser. No. 925,625 filed July 17, 1978, now abandoned.

This invention relates to a new process and more particularly it relates to a process for the manufacture of p-hydroxyphenylglycine (2-amino-2-p-hydroxyphenylacetic acid).

It is known from United Kingdom specification Nos. 1,353,612 and 1,371,896 that p-hydroxyphenylglycine may be obtained by the condensation of phenol, glyoxylic acid and ammonia. Many examples of this process are described, but in neither specification is a yield higher than 50% recorded. We have repeated this work, and we confirm that the yield of p-hydroxyphenylglycine obtained is generally about 35% and that this yield cannot substantially be improved. Furthermore, in order to obtain this yield a substantial excess of phenol is required. It is stated in specification No. 1,371,896 that the glyoxylic acid reacts initially with the ammonia, and that this reaction product then reacts with the phenol.

In commonly assigned U.S. application Ser. No. 908,465, filed May 22, 1978, there is described a convenient method of obtaining p-hydroxymandelic acid (2-hydroxy-2-p-hydroxyphenylacetic acid) in the form of its solid sodium salt. This salt is easily separated from organic impurities and is obtainable in high yield.

We have now found, and herein lies our present invention, that the said sodium salt may be converted into p-hydroxyphenylglycine in high yield, under preferred conditions in greater than 90% yield.

p-Hydroxyphenylglycine is a valuable intermediate of use in the pharmaceutical industry. It is useful in the preparation of amoxycillin, which is its amide with 6-aminopenicillanic acid, and also it is useful, as described in commonly assigned co-pending U.S. application Ser. No. 908,465, in the preparation of p-hydroxybenzyl cyanide, the value of which is described in said co-pending application.

According to the invention there is provided a process for the manufacture of p-hydroxyphenylglycine or an N-alkyl or N,N-dialkyl derivative thereof which comprises the reaction of p-hydroxymandelic acid or a salt thereof with ammonia or an alkyl- or dialkylamine or a salt thereof.

A suitable alkyl- or dialkylamine is, for example, such an amine where the one or two alkyl groups have up to 6 carbon atoms, for example methylamine, dimethylamine or diethylamine.

Preferably the p-hydroxymandelic acid is used as an alkali metal salt thereof, particularly the sodium salt, and preferably the ammonia or amine is used predominantly as an acid-addition salt thereof, for example a chloride, sulphate or acetate salt. However, it is preferable that some free ammonia or amine be present either as such or by hydrolysis of a salt with a weak acid such as acetic acid.

The reaction is conveniently carried out in aqueous solution at an elevated temperature, preferably in boiling water at 100° C. or even at a higher temperature, for example up to 135° C., at a higher than atmospheric pressure in a sealed vessel, for example at a pressure of up to 25 pounds per square inch.

It is postulated that the high yield is obtained because under preferred conditions where both the p-hydroxymandelic acid and the ammonia or amine are used as salts thereof, but some free ammonia or amine is present, the solute concentration in and pH of the reaction medium are such that the desired product is sparingly soluble and is therefor continuously precipitated from the medium. The equilibrium of the amino radical and hydroxy radical exchange reaction is therefore continuously being displaced in the desired direction.

The invention is illustrated but not limited by the following Examples:

EXAMPLE 1

A mixture of sodium p-hydroxymandelate monohydrate (10.6 g.), ammonium chloride (5.35 g.), concentrated aqueous ammonium hydroxide solution (0.5 ml.) and water (10 ml.) is stirred and heated under reflux (internal temperature 114° C.) for 21 hours. The solid product continuously precipitates from the solution during this time. Water (15 ml.) is added and the mixture is stirred, cooled and then filtered. The solid residue is washed three times with water (2 ml. each time) and then copiously with acetone. There is thus obtained p-hydroxyphenylglycine (6.91 g., 83% yield), m.p. 225°–227° C. (with decomposition). The product is shown to be free from contamination with ammonium chloride by means of a test with aqueous silver nitrate solution.

The combined filtrate and aqueous washings are concentrated to 17 ml., concentrated aqueous ammonium hydroxide solution (0.25 ml.) is added and the mixture is stirred and heated under reflux for 20 hours. The mixture is diluted with water (13 ml.), cooled, adjusted to pH 5 with acetic acid and then filtered. The solid residue is washed twice with water (2 ml. each time) and then copiously with acetone, and there is thus obtained a further 0.66 g. of p-hydroxyphenylglycine, bringing the total yield to 91%.

EXAMPLE 2

A mixture of sodium p-hydroxymandelate monohydrate (1.04 g.), ammonium acetate (2.0 g.) and water (0.5 ml.) is stirred and heated under reflux (internal temperature 125° C.) for 2.5 hours. Water (3 ml.) is added to the thick slurry thus obtained, the mixture is cooled and filtered and the solid residue is washed twice with water and then with acetone. There is thus obtained p-hydroxyphenylglycine (0.56 g., 66% yield).

EXAMPLE 3

A mixture of sodium p-hydroxymandelate monohydrate (2.08 g.), ammonium sulphate (13.2 g.), concentrated aqueous ammonium hydroxide solution (1 ml.) and water (15 ml.) is stirred and heated under reflux (internal temperature 103° C.) for 30 hours. Water (10 ml.) is added to the thick hot slurry thus obtained, and the mixture is then cooled and filtered. The solid residue is washed with water and acetone and there is thus obtained p-hydroxyphenylglycine (1.08 g., 65% yield).

EXAMPLE 4

A mixture of sodium p-hydroxymandelate monohydrate (52.0 g.), ammonium chloride (37.5 g.), concentrated aqueous ammonium hydroxide solution (2.5 ml.) and water (40 ml.) is stirred and heated at 135° C. in a sealed vessel under a pressure of 22 pounds per square inch for 4 hours. The temperature is reduced to 100° C., the pressure is returned to atmospheric pressure and cold water (75 ml.) is added. The mixture is cooled to 15°–20° C., stirred for 30 minutes and then filtered. The solid product is washed twice with water (50 ml. and 25 ml. respectively), then with acetone and dried at 70° C. There is thus obtained p-hydroxyphenylglycine (37.6 g., 90% yield).

What we claim is:

1. A process for the manufacture of p-hydroxyphenylglycine or an N-alkyl or N,N-dialkyl derivative thereof which comprises the reaction of p-hydroxymandelic acid or a salt thereof with ammonia or an alkyl- or dialkylamine or a salt thereof in aqueous solution at a temperature of between 100° and 135° C.

2. A process as claimed in claim 1 wherein the alkyl- or dialkylamine is such an amine where the one or two alkyl groups have up to 6 carbon atoms.

3. A process as claimed in claim 2 wherein the amine is methylamine, dimethylamine or diethylamine.

4. A process as claimed in claim 1, wherein the p-hydroxymandelic acid is used as an alkali metal salt thereof.

5. A process as claimed in claim 4 wherein the salt is the sodium salt.

6. A process as claimed in claim 1 wherein the ammonia or amine is used predominantly as an acid-addition salt thereof.

7. A process as claimed in claim 6 wherein the salt is the chloride, sulphate or acetate salt.

8. A process as claimed in claim 1 wherein some free ammonia or amine is present.

9. A process for the manufacture of p-hydroxyphenylglycine according to claim 1 which comprises the reaction of sodium p-hydroxymandelate with ammonia and an ammonium salt in aqueous solution at a temperature of between 100° and 135° C.

10. A process for the manufacture of p-hydroxyphenylglycine or an N-alkyl or N,N-dialkyl derivative thereof which comprises heating a mixture of the sodium salt of p-hydroxymandelic acid, ammonium salt and concentrated aqueous ammonium hydroxide to a temperature between 100° and 135° C. and separating and washing the resulting solid residue.

11. A process for the manufacture of p-hydroxyphenylglycine or an N-alkyl or N,N-dialkyl derivative thereof which comprises heating at a temperature of 100° to 135° C. an aqueous solution of alkali metal salt of p-hydroxymandelic acid and ammonia or alkyl- or dialkyl-amine, wherein the ammonia or amine are present primarily in the form of an acid addition salt thereof, but with some free ammonia or free amine also being present, the desired product being continuously precipitated out of the solution to give a product yield in excess of 90%.

12. A process according to claim 1 which comprises refluxing a mixture of sodium p-hydroxymandelate, an ammonium salt selected from the group consisting of ammonium chloride, ammonium sulphate and ammonium acetate, ammonium hydroxide and water, collecting the precipitated product constituting p-hydroxyphenylglycine and washing the same with water.

* * * * *